United States Patent
Vitulano et al.

(10) Patent No.: US 10,041,872 B2
(45) Date of Patent: Aug. 7, 2018

(54) METHOD FOR EVALUATING THE CLEANING STATE OF AN AERATION AND/OR CONDITIONING PLANT OF A ROOM

(71) Applicants: CONSIGLIO NAZIONALE DELLE RICERCHE, Rome (IT); TAGLIAFERRI S.r.l., Rome (IT); Fabio Buccolini, Rome (IT)

(72) Inventors: Domenico Vitulano, Rome (IT); Daniela De Canditiis, Rome (IT); Vittoria Bruni, Rome (IT); Sante Tagliaferri, Rome (IT); Fabio Buccolini, Rome (IT); Elisa Rossi, Rome (IT); Daniele Pigozzi, Rome (IT)

(73) Assignees: CONSIGLIO NAZIONALE DELLE RICERCHE, Rome (IT); TAGLIAFERRI S.R.L., Rome (IT); FABIO BUCCOLINI, Rome (IT)

( * ) Notice: Subject to any disclaimer, the term of this patent is extended or adjusted under 35 U.S.C. 154(b) by 0 days.

(21) Appl. No.: 15/027,694

(22) PCT Filed: Sep. 30, 2014

(86) PCT No.: PCT/IB2014/064943
§ 371 (c)(1),
(2) Date: Apr. 6, 2016

(87) PCT Pub. No.: WO2015/052617
PCT Pub. Date: Apr. 16, 2015

(65) Prior Publication Data
US 2016/0238507 A1 Aug. 18, 2016

(30) Foreign Application Priority Data
Oct. 7, 2013 (IT) .............................. RM2013A0547

(51) Int. Cl.
*G01N 15/06* (2006.01)
*B01D 46/00* (2006.01)
(Continued)

(52) U.S. Cl.
CPC ...... *G01N 15/0618* (2013.01); *B01D 46/0086* (2013.01); *B08B 13/00* (2013.01);
(Continued)

(58) Field of Classification Search
CPC .. F24F 2011/0093; B01D 46/42; B08B 13/00; G01N 2001/028; G01N 2015/0096
See application file for complete search history.

(56) References Cited

U.S. PATENT DOCUMENTS

| 9,366,448 B2 * | 6/2016 | Dean-Hendricks ... F24F 3/1603 |
| 2003/0070544 A1 * | 4/2003 | Mulvaney .......... B01D 46/0086 95/25 |

(Continued)

FOREIGN PATENT DOCUMENTS

| JP | H10-170423 | 6/1998 |
| JP | 2003-106981 | 4/2003 |

OTHER PUBLICATIONS

Ahmad, Irtishad, Berrin Tansel, and Jose D. Mitrani. "Effectiveness of HVAC duct cleaning procedures in improving indoor air quality." Environmental monitoring and assessment 72.3 (2001): 265-276.*

(Continued)

*Primary Examiner* — Lisa Caputo
*Assistant Examiner* — Punam Roy
(74) *Attorney, Agent, or Firm* — Arent Fox LLP (57) ABSTRACT

The present invention places in the field of the maintenance of aeration, conditioning, air-conditioning, etc. plants, and in particular the present invention relates to a method for evaluating the cleaning state of a plant, with particular reference to the atmospheric particulate.

20 Claims, 3 Drawing Sheets

(51) Int. Cl.
*G01N 15/00* (2006.01)
*F24F 11/00* (2018.01)
*B08B 13/00* (2006.01)
*G01N 1/02* (2006.01)
*F24F 11/39* (2018.01)

(52) U.S. Cl.
CPC ........... G01N 1/02 (2013.01); G01N 15/0625 (2013.01); *F24F 11/39* (2018.01); *G01N 2001/028* (2013.01); *G01N 2015/0046* (2013.01); *G01N 2015/0049* (2013.01); *G01N 2015/0096* (2013.01)

(56) References Cited

U.S. PATENT DOCUMENTS

| | | | | |
|---|---|---|---|---|
| 2011/0061527 | A1* | 3/2011 | Sullivan | B01D 46/18 95/1 |
| 2011/0185895 | A1* | 8/2011 | Freen | G01N 15/08 95/25 |
| 2012/0297974 | A1* | 11/2012 | Hwang | B01D 46/42 95/1 |
| 2012/0318073 | A1* | 12/2012 | Zavodny | B01D 46/0086 73/862.581 |
| 2012/0318137 | A1* | 12/2012 | Ragland | B01D 46/42 95/25 |
| 2013/0158717 | A1* | 6/2013 | Zywicki | F24F 11/0086 700/276 |
| 2014/0208942 | A1* | 7/2014 | Scipio | B01D 46/0086 95/1 |
| 2015/0260424 | A1* | 9/2015 | Fadell | F24F 11/0012 236/1 C |

OTHER PUBLICATIONS

Basile, M. C., et al. "Automatic and Noninvasive Indoor Air Quality Control in HVAC Systems." Journal of Industrial Mathematics 2016 (2016).*

Zhou, Bin, Bin Zhao, and Zhongchao Tan. "How particle resuspension from inner surfaces of ventilation ducts affects indoor air quality—A modeling analysis." Aerosol Science and Technology 45.8 (2011): 996-1009.*

International Search Report for PCT/IB2014/064943, five pages, (dated Nov. 2014).

Written Opinion of the ISA for PCT/IB2014/064943, eight pages, (dated Nov. 2014).

Wang et al. "An experimental study on short-time particle resuspension from inner surfaces of straight ventilation ducts" *Building and Environment*, vol. 53, pp. 119-127 (Jan. 2012).

* cited by examiner

METHOD FOR EVALUATING THE CLEANING STATE OF AN AERATION AND/OR CONDITIONING PLANT OF A ROOM

This application is the U.S. national phase of International Application No. PCT/IB2014/064943, filed 30 Sep. 2014, which designated the U.S. and claims priority to Italian Application No. RM2013A000547, filed 7 Oct. 2013; the entire contents of each of which are hereby incorporated by reference.

The present invention places in the field of the maintenance of aeration, conditioning, air conditioning, etc. plants.

In particular, the present invention relates to a method for evaluating the cleaning state of a plant, with particular reference to the atmospheric particulate.

The atmospheric particulate, also called atmospheric aerosol or more simply powders, is constituted by a mixture of organic and inorganic substances, the origin thereof can depend both upon processes linked to the anthropic activity and upon natural processes and it can take place both for the direct release and for the formation in atmosphere after reactions involving other substances.

The interest which has created around these compounds, in particular the thinnest fraction thereof ($PM_{10}$, that is microscopic particles the aerodynamic diameter thereof is equal or smaller than 10 μm) which can be absorbed more easily by the organism, is due to the dangerousness thereof for the human health. If on one side these powders can result to be intrinsically toxic, based upon the specific chemical-physical features of the substances composing them, on the other side they can act as vehicle carrying still more dangerous and toxic absorbed substances, such as the organic micropollutants or heavy metals as also documented by the WHO (World Health Organization) which estimates as 30% the rate of illnesses linked to the poor air quality in subjects housed in not residential rooms.

Then, it is particularly important to do a good maintenance of the plant so that both the air-distributing ducts and the filters are always clean.

On the other side, there is the need of understanding, in time, when in an efficiency and effectiveness optics it is necessary to do an intervention for cleaning the ducts and/or cleaning and/or replacing the filters.

Up to now this is performed based upon predetermined time intervals, at fixed frequency, or upon (direct or indirect) measurements of the powder concentration upstream and/or downstream of the filter and, in each case, all directed to evaluate the efficiency of the filters only.

However, it is also important to monitor the cleaning state of the plant ducts wherein, during time, powders accumulate which can be then released inside the room assisted by the plant or favour the proliferation of fungi and bacteria in the ducts themselves.

On the other side, the measurements for evaluating the powder concentration inside the ducts of a plant necessarily are of invasive type and then they provide expensive demanding interventions and consequently plant stopping moments which, due to the measurement nature, can even result to be particularly long with clear decrease in the use of the rooms assisted by the plant.

The object of the present invention then is to overcome the above-illustrated problems and this is obtained by an evaluation method as defined by claim 1.

The present invention, by overcoming the problems of the known art, involves several and clear advantages.

First of all, the present invention is practical and cheap to be implemented.

It has the advantage of implementing a portable and robust protocol able to determine the plant cleaning state starting from few measurements performed locally at fixed time instants.

Furthermore, it is an absolutely not invasive method as all necessary measurements are performed outside the plant, without requiring technical and/or plant stopping interventions.

Furthermore, the present invention allows evaluating, independently, both the cleaning state of the ducts, and the cleaning state of the filters. A combined reading of the method results can then provide complete and exhaustive information about the general cleaning state of the plant, about the presence of powders, in particular of thin powders ($PM_{10}$) and about the need of maintenance and cleaning interventions on ducts and/or filters.

Notwithstanding the invention proposes a punctual (in the time sense) check of the plant state and of the cleaning conditions of the same, the mathematical model underlying the used calculation algorithms even allows to make a forecasting estimate about the intervention time for the maintenance and cleaning of the ducts and/or filters.

The forecasting estimates could be then able to establish the optimum intervention time to guarantee the correct plant maintenance based upon its historical series of measurements.

These and other advantages, together with the features and use modes of the present invention, will result evident from the following detailed description of preferred embodiments thereof, shown by way of example and not with limitative purpose.

The figures of the enclosed drawings will be referred to, wherein.

Figure 1A:
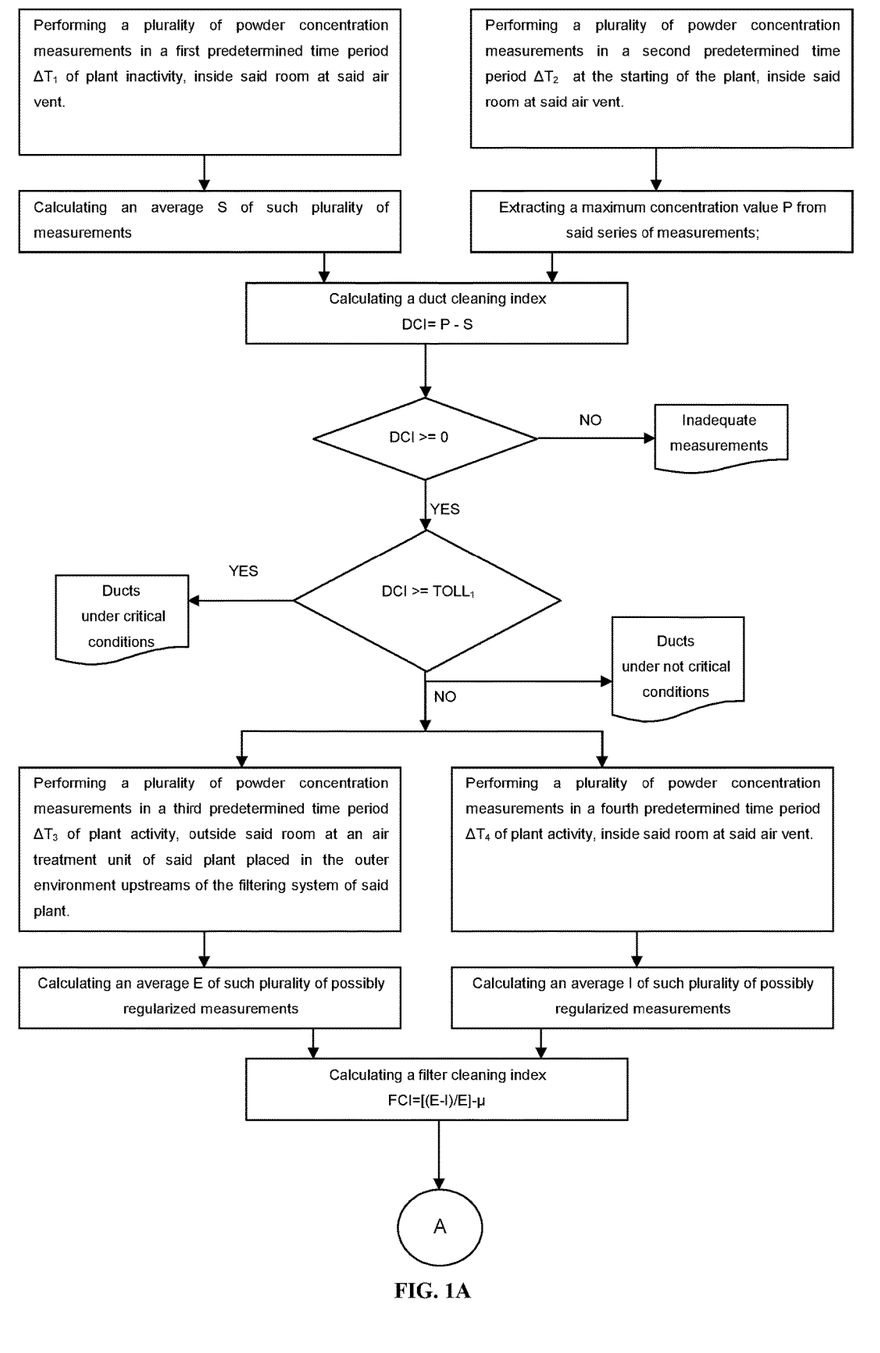
FIGS. 1A and 1B are flow charts indicating the method according to the present invention.
Figure 1B:
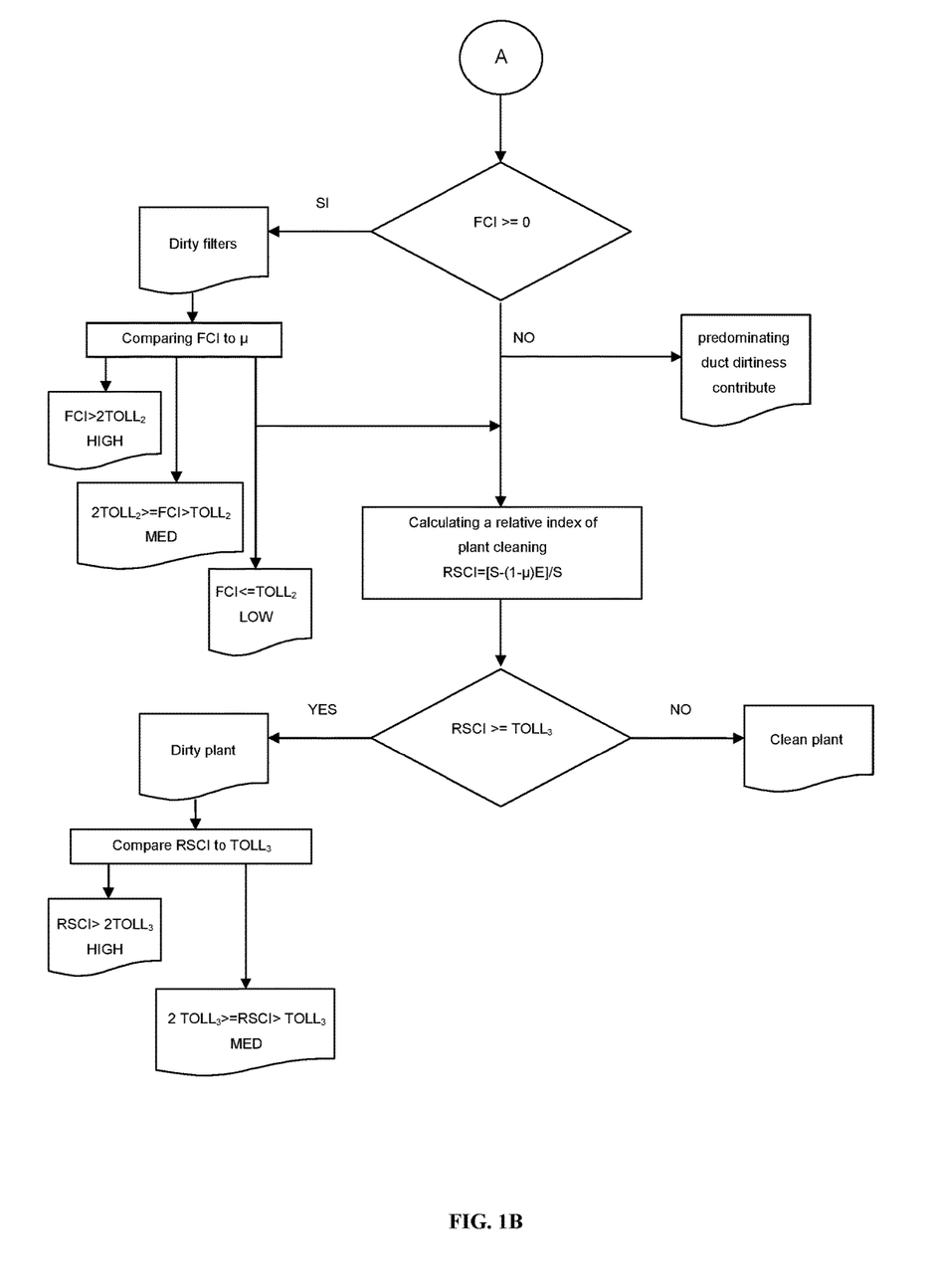
Figure 2:
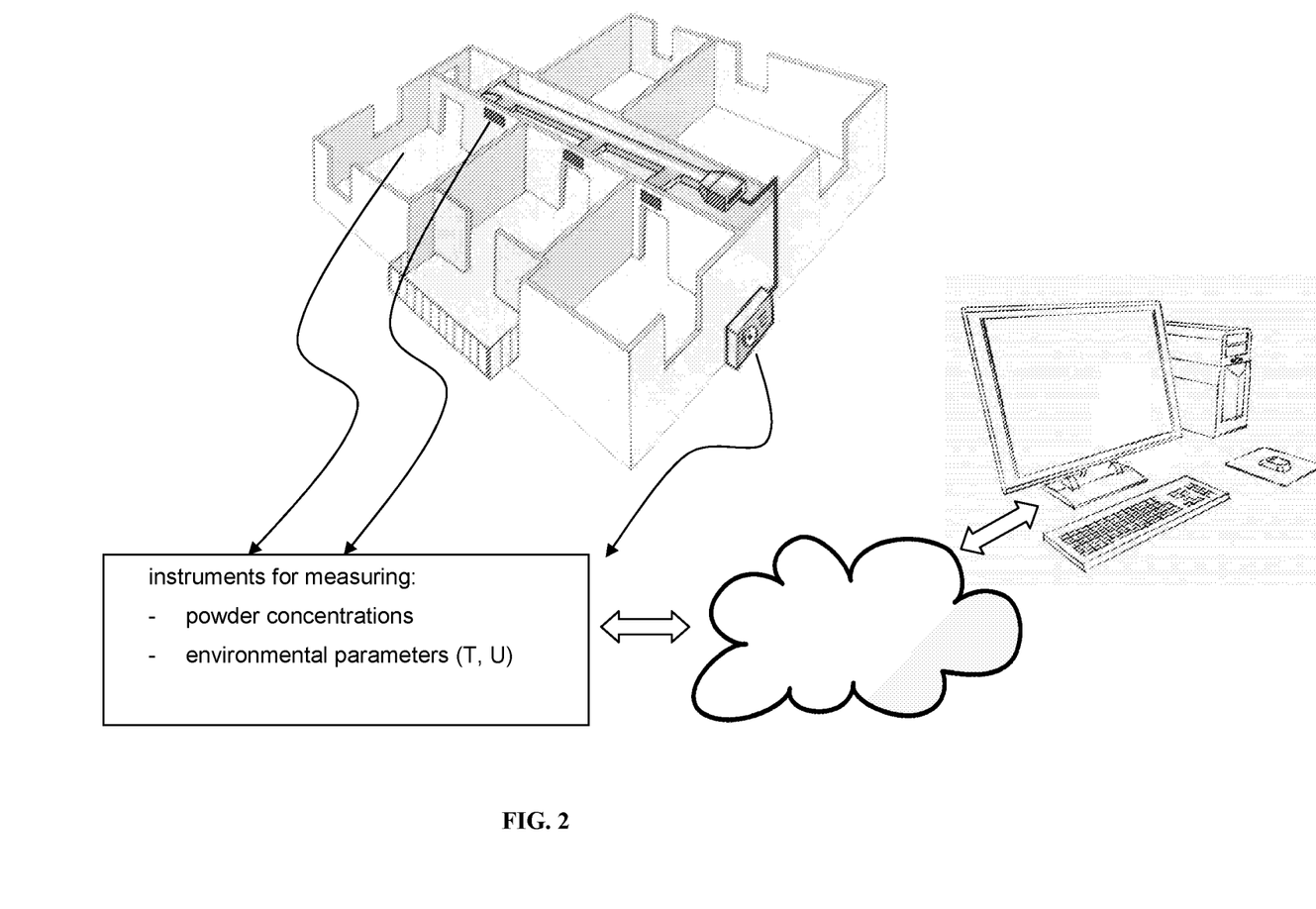
FIG. 2 is an exemplifying scheme of the system for evaluating the cleaning state of an aeration/conditioning plant as considered in the present invention.

By assuming a well-operating plant, under state the functionality of the filter components and the level of inner cleaning of the plant itself is meant. The aeration and/or conditioning plant is assimilated to a system wherein the air enters with a certain concentration of $PM_{10}$ (input) and outgoes at the plant air vent with another concentration of $PM_{10}$ (output) (compare FIG. 2).

Supposing that the plant is calibrated with respect to the volumetry and to the use destination of the building, the quality of the air input by the plant into the inner environment strongly depends upon the correct maintenance and cleaning of the filters and of the plant itself.

If the plant was an insulated system and if the quantity of the input $PM_{10}$ was constant, one could easily evaluate the overall efficiency of the plant with the following ratio $$(PM_{10}(input) - PM_{10}(output))/PM_{10}(input).$$

It is obvious that the assumption of the insulated system is not plausible and therefore the efficiency has to be calculated by taking into consideration that the input quantity of $PM_{10}$ is very variable and depends upon several factors. Therefore, the plant efficiency cannot be evaluated by using an instantaneous "photo" of the values at issue only, but it is to be obtained by considering the $PM_{10}$ values mediated in a suitable span and trying to take into account the influence of other factors as much as possible.

The $PM_{10}$ concentration is a very variable quantity which depends both upon natural factors (powder, earth, marine salt raised by the wind, fires, microorganisms, pollens and e spores, rock erosion, volcanic eruptions, cosmic powder) and by anthropic factors (emissions of the combustion of engines, emissions of the domestic heating, residues of the wear of road surface, brakes and vehicle tyres, emissions of mechanical processings, cement works, building sites, agricultural processings, burners and power plant, tobacco smokes).

As confirmed by the several measurement campaigns performed by institutions, agencies and by the local organizations in charge apart from by the experimentation itself performed within the present invention, the natural and anthropic factors being equal, the measurement of $PM_{10}$ concentrations even depends upon meteorological factors such as temperature, humidity, atmospherical pressure and wind.

The plurality of the variables at stake makes the evaluation of the cleaning state of the plant system rather complex in a monitoring context wherein all variables must be measured experimentally.

For this reason in the present invention a functional model has been defined which reduces the independent variable as much as possible, by concentrating on the more objective ones, to be measured more easily.

Any commercial hygrometer measures the relative humidity, defined as the ratio between the existing vapour in a given air volume and the one which would be if this was sature. Therefore a humidity of 100% means that the air contains the maximum quantity of water vapour at that temperature and at that atmospherical pressure. In meteorology the saturation point of the water vapour in the air is called indeed dew point and, the atmospherical pressure being equal, it is designated as Tr. Since the following empiric law of Magnus-Tetens is valid $$\frac{17,27\,Tr}{237,7+Tr} = \frac{17,27\,T}{237,7+T} + \ln(U/100)$$

which represents a constraint between dew temperature (and then pressure), temperature (T) and relative humidity (U), out of the three meteorological variables only two of them can be measured and furthermore, as temperature and humidity can be measured easily, the following functional model can be defined $$C(t)=f(T(t);U(t));$$

wherein the wind variable is supposed to be constant in the span wherein the measurements are performed. The time variables C(t), T(t) and U(t) represent the concentrations of powders (for ex. of $PM_{10}$), temperature and relative humidity, respectively, measured in a specific time period [t0; tn].

All other quantities, which can influence the measurement C(t), are meant to be incorporated in the functional model. Therefore it should have to be assessed starting from the experimental data related to the plant in order to be able to incorporate as much accurately as possible the influence and the variability of the natural and anthropic factors of the considered context.

As the quality of the estimation of a functional model is strongly linked to the ratio between number of measurements and number of unknown parameters to be estimated, the choice of the functional model preferably falls on a simple model with few parameters. Furthermore, having measured a strong linear correlation between C(t) and U(t), the chosen model is of linear type.

More precisely, having defined $(\alpha, \beta, \gamma) \in R^3$, the following relationship is defined:

$$C(t)=\alpha U(t)+\beta T(t)+\gamma$$

wherein the parameters $\alpha$, $\beta$, $\gamma$ are estimated starting from a set of time measurements performed in the analysis site and they will be specific and characterizing the site at issue. From this latter point one understands that the possibility of monitoring the same plant in time can refine the reliability of the estimation of the parameters characterizing the plant inserted in its geographical/environmental context and lead to more reliable forecasting estimations.

According to a preferred embodiment of the present invention, the process for evaluating the cleaning state of an aeration and/or conditioning plant of a room, first of all provides to perform a first powder concentration measurement S, obtained as average of a plurality of powder concentration measurements performed in a first predetermined time period $\Delta T_1$ of plant inactivity, inside the room at an air vent inside the room itself.

Although it is considered possible to perform such first measurement at any emission air vent of the plant, in case there is more than one of them, it is considered preferable performing the measurement at the most distant one from the air treatment unit, which presumably, is assisted by a longer tract of ducts.

Furthermore, in order to make the measurement as much reliable as possible, it is preferable performing the measurement at the distance from the air vent which is not able to invalidate the measurement itself or which does not tend to evaluate the powder concentrations in the room and which thus does not exceed 10 centimeters from the air vent itself.

Such first predetermined time period of plant inactivity $\Delta T_1$, during thereof the first powder concentration measurement S is performed, preferably is a quite long period of time, for example comprised between about 6 and 12 hours. Such time interval, as it will be clear hereinafter, preferably can be chosen in a period wherein the temperature difference between the outer environment and the room interior results to be negative.

Temperature measurements inside the room Ti and in the outer environment Te can be then provided, so that the first predetermined time period of plant inactivity $\Delta T_1$ is set in a period wherein Te<Ti.

Furthermore, as a time period has to exist wherein the plant is stopped, one prefers to set it at night.

Still to better perform the measurements, so that these are not influenced by different and not assessable factors, it is preferable that during such measurement period $\Delta T_1$, the room has closed doors and/or windows. Furthermore, it is also preferable that the room itself is in a cleaning state so as not to have a high powder concentration and/or other particulate of different type from the considered one which could alter the measurements themselves.

The process then provides to perform a series of powder concentration measurements during a second predetermined time period $\Delta T_2$, at the starting of the plant. The series measurements, during such second time interval $\Delta T_2$ are performed once again inside the room at the same air vent.

Such second predetermined time period $\Delta T_2$, preferably comprises the plant starting instant and it has a duration preferably comprised between $\pm\frac{1}{4}$ hour and $\pm 1$ hour with respect to the plant starting instant.

Advantageously, the time period $\Delta T_2$ is chosen as substantially consecutive to the first predetermined time period of plant inactivity $\Delta T_1$.

From the series of performed measurements, a concentration maximum value P should have to be extracted.

At this point, a first duct cleaning index DCI of the plant can be calculated as difference between the concentration maximum value P and the first concentration measurement S.

It was tested that the DCI duct cleaning index is indicative of the quantity of powders contained in the ducts and therefore it represents a cleaning state of the ducts themselves.

In particular, it designates a state of critical dirtiness if it results greater or equal to a first predetermined threshold value $TOLL_1$, wherein such first threshold value $TOLL_1$ advantageously can be chosen up to a maximum of about 0.05 mg/m$^3$.

For supporting the proposed methodology there is the consideration that after shutting off the plant, during the whole inactivity period, for example the night, in the aeration/conditioning plant a chimney effect is created, a natural ventilation phenomenon inside the building caused by the temperature difference between the inner environment and the outer environment.

During such periods, in fact, a considerable variability of the inner powder concentration data was observed, due to the convective motions developed by the motion of air which is sucked by the air vent of the plant and causes, indeed, the chimney effect. This observation allows supposing that at time of starting the plant the maximum concentration peak of $PM_{10}$ is reasonably due to the average of concentration of powder sucked back at the air vent during the inactivity period from the room and due to what has accumulated during time in the ducts of the plant itself.

By designating with S the powder concentration average measured during the inactivity period, for what said one expects that P–S is always a positive quantity. In the different measurements performed on a sample plant, this results to be true in more than 80% of the cases. The cases therein the P–S difference results to be negative are the days wherein the powder in the room, due to unpredictable reasons and causes, results to be on the average much higher than the treated quantities and it makes the measurement inadequate for the described analysis.

This is the reason why in the advice for performing the process, it is recommended that the measurements are performed in a clean room wherein doors and windows are left closed during the measurement day.

Assuming that the measurement is reliable and then DCI=P–S is greater than zero, this value, which represents the powder quantity contained in the ducts, is compared to the maximum tolerance threshold, for example a threshold established by the law.

In case wherein P–S<$TOLL_1$, that is the powder quantity contained in the ducts is lower than the established threshold, one can try anyway to quantify the powder quantity contained in the ducts in relation both to the powder quantity of the outer environment and the powder quantity which at operating speed is input in the room from the plant, in order to supply additional information.

A first evaluation of the global plant efficiency is obtained upon considering the profiles of powder concentration in the outer environment and the profiles of powder concentration inside the room.

In particular, according to an embodiment of the present invention, the process further comprises a step of performing a third powder concentration measurement E, obtained as an average of a plurality of powder concentration measurements performed during a third predetermined time period $\Delta T_3$ of plant activity, outside said room, at an air treatment unit of said plant placed in the outer environment, upstream of the filtering system of said plant.

Furthermore, such embodiment provides a step of performing a fourth powder concentration measurement I, obtained as average of a plurality of powder concentration measurements performed in a fourth predetermined time period $\Delta T_4$ of the plant activity, inside said room at said air vent.

Preferably, the third predetermined time period $\Delta T_3$ and the fourth predetermined time period $\Delta T_4$ are chosen so as to result substantially coincident, or can be approximated to substantially coincident time intervals.

Furthermore, it is preferable that such third time period $\Delta T_3$ and fourth time period $\Delta T_4$ are subsequent by at least ¼ hour with respect to the starting of the plant, in order to avoid that the before-calculated concentration peak P falls inside thereof.

As the global efficiency of the plant is evaluated by means of the following formula $$(E-I)/E,$$

according to such embodiment, a filter cleaning index FCI is calculated as:

$$FCI=[(E-1)/E]-p,$$

wherein μ represents a nominal value for the filter efficiency. Such filter cleaning index FCI, as it will be clear hereinafter, is indicative of a state of dirty filter if it results to be greater than zero.

For example, when the filter cleaning index FCI results to be greater than zero, a step of comparing the filter cleaning index FCI to the nominal value for the filter efficiency μ can be provided, for classifying the critical state of the filter among two or more criticism classes defined as percentages of the nominal value for the filter efficiency μ.

Therefore, for example, growing critical states can be defined if FCI is compared to a threshold value $TOLL_2$ which can be advantageously chosen equal to 0.05μ:

FCI is greater than or equal to $TOLL_2$,

FCI is greater than $TOLL_2$ and lower than or equal to $2TOLL_2$,

FCI is greater than 2 $TOLL_2$.

In what precedes, it is preferable that such third time period $\Delta T_3$ and fourth time period $\Delta T_4$ correspond to stationary meteorological conditions.

The preceding definition of the filter cleaning index is based upon the following considerations.

In the phase of planning an aeration/conditioning plant, based upon the volumetry and the use destination of the room, the air flow necessary to keep the right air exchange is established. The flow is defined as air cubic meters per surface unit and therefore given a certain filtering surface the speed v of the air flow remains determined.

Once established the air speed v, for the filtering system the following ratio is valid $$\Delta Pr=KEv^2t+Rv$$

wherein ΔPr is the pressure difference upstream and downstream of the filtering system (called pressure loss), K is the specific resistance of the powder, E is the powder concentration in the outer environment upstream of the filter and R is the resistance of the clean filter.

The parameters of the previous equation have been assessed experimentally on pilot plants and they are used by the manufacturers to establish the intervention time for the filter replacement as well as the maximum time tmax needed so that the pressure loss ΔPr is the maximum allowed one. By solving the equation with respect to time, an estimate of tmax is obtained given by the following identity $$tmax=(\Delta Pr-Rv)/(KEv^2).$$

Therefore the average lifetime of a filter is inversely proportional to the quantity of powder E outside the plant itself.

From this observation it is deduced that the intervention time for the maintenance of the same filter can vary depending upon the working conditions of the same. Practically the pressure loss in time is inversely proportional to the quantity E as it is due to the clogging of the filter itself and therefore the pressure loss is accompanied by an increase in the retention efficiency. In fact, it is known that the air filters are less efficient when they are new and increase their efficiency in time.

Therefore, if μ(t) is the filter retention efficiency versus time, for what has been said μ(t) is a function increasing in time and μ(0)=μ is the efficiency of the just replaced new filter.

In the scope of the present invention, the powder concentration downstream of the plant I can be considered as the sum of the two following contributions:

(1−μ(t))E which represents the powder concentration not kept by the filter and Cimp(t) which represents in absolute terms the powder contribution of the plant itself. Therefore, the global efficiency can be re-written as the algebraic sum of two components $$(E-I)/E=[E((1-\mu(t))E+Cimp(t))]/E=\mu(t)-Cimp(t)/E.$$

Of course, the profiles at issue can be considered both as the regularized values obtained in a span of one or more days, and be considered in long-term monitoring optics.

The proposed estimation of the plant global efficiency is then used to test the maintenance state of the plant itself. In fact, under optimum maintenance conditions the plant global efficiency is given by the filter efficiency. If μ∈(0; 1), the filter retention efficiency (e.g. a filter with medium efficiency has μ=0.75) this is the expected value of the plant global efficiency when the filter is well operating and the plant cleaning is adequate.

In fact in such case the inner measurement is given exclusively by the quantity of powders which succeeds in overcoming the filter, and then I=(1−μ)E, thereafter it follows that the global efficiency coincides with the filter retention efficiency μ . . . .

The deviation of the plant global efficiency from the expected value μ is an index of an inadequate maintenance which could be attributed both to the bad operation of the filter and to the cleaning level of the plant itself.

In particular:

FCI>0 denotes a compromise of the plant filter component;

FCI<0, on the contrary, denotes that the decrease in the global efficiency must be surely attributed to the bad cleaning of the ducts in the plant.

Moreover, if one wants to provide the possibility of monitoring in time the conditioning plant, in order to make year periods comparable therebetween and to keep into consideration as much as possible the influence of the meteorological/environmental factors which in a brief period can consider to be constant, a method is proposed able to consider the effects of the meteorological and environmental conditions by extrapolating the trend of the measurements in the exterior and the trend of the measurements in the interior and by considering them as the quantities to be compared for evaluating the global efficiency.

To this purpose it is possible providing a step of regularizing the third powder concentration measurement E and the fourth powder concentration measurement I with respect to temperature and/or humidity values measured in the respective measurement time points and intervals.

To this purpose, then, it is advantageous regularizing the temperature and humidity profiles by integrating such quantities in time [t0; : : : ; tn] and obtaining humidity $U_E$ and temperature $T_E$ average values in the exterior and $U_1$ and $T_1$ in the interior.

In this way it is possible regularizing the powder concentration measurement E made in the outer environment by using the functional model described previously:

$$E=\alpha_E U_E+\beta_E T_E+\gamma_E$$

wherein $\alpha_E$, $\beta_E$, $\gamma_E$ are obtained by means of a least-square estimation and that is as the solution of the functional of fitting $$\mathrm{argmin}_{(\alpha,\beta,\gamma)}\|E-(\alpha U_E+\beta T_E+\gamma)\|^2.$$

Analogously, the trend of $PM_{10}$ concentrations in the interior can be estimated by using the same functional model wherein, however, the humidity is mediated between the outer and inner values which result to be almost constant as linked to the room exposition and to the temperature of the same and therefore very little variable.

Therefore it is defined $$I=\alpha_1(U_E+U_I)/2+\beta T_I+\gamma\|^2.$$

being $$(\alpha_I,\beta_I,\gamma_I)=\mathrm{argmin}_{(\alpha,\beta,\gamma)}\|I-(\alpha(U_E+U_I)/2+\beta T_I)\|^2.$$

According to an embodiment of the present invention, a step of calculating a plant cleaning relative index RSCI as $$RSCI=[S-(1-\mu)E]/S,$$

can be further provided, wherein the plant cleaning relative index RSCI is indicative of a dirty plant when it results to be higher or equal to a third predetermined threshold value $TOLL_3$.

For example, such third threshold value $TOLL_3$ can be chosen equal to about 0.15.

Furthermore a step of comparing the plant cleaning relative index RSCI to the third threshold value $TOLL_3$, can be performed advantageously for classifying the critical state of the plant among two or more criticism classes defined as percentages of the third predetermined threshold value $TOLL_3$.

Then, for example, growing critical states if:

RSCI is greater than or equal to $TOLL_3$,

RSCI is greater than $TOLL_3$ e lower than or equal to 2 $TOLL_3$,

RSCI is greater than 2 $TOLL_3$.

An additional subject of the present invention is then a system able to implement the process described up to now and suitable then to process data of measurements to obtain the cleaning indexes as above defined and described and then to provide the operator an indication about the need/opportunity of performing maintenance operations on the plant.

The system can then provide measurement instruments to measure environmental parameters such as temperature and humidity (therefore probes, sensors, etc.).

Furthermore, the system should comprise instruments (probes, sensors, etc.) for measuring (directly or indirectly) the concentration of powders, in particular for $PM_{10}$.

It is to be meant that to the purpose the most varied technologies could be used, both for measurement timing, instrument implementation, data transfer, etc.

The data coming from the measurement instruments could be then acquired in a processing unit which, properly programmed, could provide for the necessary calculations, data storage, both numerical and visual presentation thereof by means of simple and intuitive means.

It is to be meant that the system architecture, the modes for receiving and transmitting data between the measurement units and the processing unit could be implemented depending upon the specific needs. For example physical connections or network connections, for example internet, can be provided.

It is to be meant that the system could be at least partially based upon a software dedicated to the implementation of one or more steps of the process as described and claimed.

The present invention has been sofar described by referring to preferred embodiments thereof. It is to be meant that each one of the technical solutions, implemented in the preferred embodiments described herein by way of example, could be combined advantageously in a different way therebetween, to create other embodiments, belonging to the same inventive core and however all within the protection scope of the here-below reported claims.

The invention claimed is:

1. A computer implemented method for evaluating cleaning status of an aeration and/or conditioning plant of a room, the plant having ducts and at least an air vent inside said room, comprising at least the steps of:
performing a first powder concentration measurement (S), obtained as an average of a plurality of powder concentration measurements performed during a first predetermined time period ($\Delta T_1$) of plant inactivity, inside said room at said air vent;
performing measurements of a first temperature (Ti) inside the room and a second temperature (Te) in outer environment to determine said first predetermined time period ($\Delta T_1$) to be set in a period where Te<Ti;
performing a series of powder concentration measurements during a second predetermined time period ($\Delta T_2$) at starting of the plant, inside said room at said air vent;
extracting a value of maximum concentration (P) from said series of measurements;
calculating a duct cleaning index (DCI) as difference between said value of maximum concentration (P) and said first concentration measurement (S);
indicating a dirty state of the ducts if said DCI is greater than or equal to a first predetermined threshold value ($TOLL_1$); and
establishing an intervention time for performing maintenance based on a value of the DCI.

2. The method according to claim 1, wherein said first predetermined threshold value ($TOLL_1$) is about 0.05 mg/m$^3$.

3. The method according to claim 1, wherein said first predetermined time period ($\Delta T_1$) is about from 6 to 12 hours.

4. The method according to claim 1, wherein during said first predetermined time period of plant inactivity ($\Delta T_1$), said room has closed doors and/or windows.

5. The method according to claim 1, wherein said second predetermined time period ($\Delta T_2$) comprises the starting of the plant.

6. The method according to claim 5, wherein said second predetermined time period ($\Delta T_2$) has a duration comprised between ±¼ hour and ±1 hour with respect to the starting of the plant.

7. The method according to claim 1, wherein said second predetermined time period ($\Delta T_2$) is substantially consecutive to said first predetermined time period of plant inactivity ($\Delta T_1$).

8. The method according to claim 1, further comprising:
performing a third powder concentration measurement (E), obtained as average of a plurality of powder concentration measurements performed during a third predetermined time period ($\Delta T_3$) of plant activity, outside said room at an air treatment unit of said plant placed in the outer environment upstream of the filtering system of said plant;
performing a fourth powder concentration measurement (I), obtained as average of a plurality of powder concentration measurements performed during a fourth predetermined time period ($\Delta T_4$) of plant activity, inside said room, at said air vent;
calculating a filter cleaning index (FCI) as:

$$FCI=[(E-I)/E]-\mu$$

wherein $\mu$ represents a nominal value for the filter efficiency, said filter cleaning index (FCI) being indicative of a dirty filter state if it is greater than zero, of a poor cleaning state of the ducts if it is lower than zero.

9. The method according to claim 8, wherein said third predetermined time period ($\Delta T_3$) and fourth predetermined time period ($\Delta T_4$) are substantially coincident.

10. The method according to claim 8, wherein said third predetermined time period ($\Delta T_3$) and fourth predetermined time period ($\Delta T_4$) are subsequent by at least ¼ hour with respect to the starting of the plant.

11. The method according to claim 8, wherein said third predetermined time period ($\Delta T_3$) and fourth predetermined time period ($\Delta T_4$) correspond to stationary weather conditions.

12. The method according to claim 8 further comprising a step of regularizing said third powder concentration measurement (E), and said fourth powder concentration measurement (I) with respect to temperature and/or humidity values measured in respective measurement points and time intervals.

13. The method according to claim 8 further comprising, when said filter cleaning index (FCI) is greater than zero, a step of comparing said filter cleaning index (FCI) with said nominal efficiency value of the filter ($\mu$), for classifying a critical state of the filter among two or more criticism classes defined as percentages of the nominal efficiency value of the filter ($\mu$).

14. The method according to claim 8 further comprising a step of calculating a plant cleaning relative index (RSCI) as:

$$RSCI=[S-(1-\mu)E]/S,$$

said plant cleaning relative index (RSCI) being indicative of a dirty plant if it is greater than or equal to a third predetermined threshold value ($TOLL_3$).

15. The method according to claim 14, wherein said third predetermined threshold value ($TOLL_3$) is about 0.15.

16. The method according to claim 14 further comprising, when said plant cleaning relative index (RSCI) is greater than or equal to said third predetermined threshold value (TOLL$_3$), a step of comparing said plant cleaning relative index (RSCI) to said third predetermined threshold value (TOLL$_3$), for classifying a critical state of the plant among two or more criticism classes defined as percentages of the third predetermined threshold value (TOLL$_3$).

17. The method according to claim 1, wherein said powders are PM$_{10}$.

18. A system for evaluating cleaning status of an aeration and/or conditioning plant of a room, adapted to implement a method according to claim 1, comprising:
   powder concentration measuring instruments;
      a processing unit, programmed so to implement one or more of the steps of the method.

19. The system according to claim 18 further comprising instruments for measuring environmental parameters including at least one of temperature or humidity.

20. The system according to claim 18 further comprising processing and interface means for numerical and/or visual presentation of processed data.

* * * * *